United States Patent
Shen

(10) Patent No.: US 6,834,554 B2
(45) Date of Patent: Dec. 28, 2004

(54) APPARATUS FOR DIRECT SHEAR STRESS TESTING OF SAMPLE

(76) Inventor: Der-Hsien Shen, 2F, No. 26, Lane 23, Hsi-Chou St., Wen-Shan Dist., Taipei City (TW)

( * ) Notice: Subject to any disclaimer, the term of this patent is extended or adjusted under 35 U.S.C. 154(b) by 0 days.

(21) Appl. No.: 10/464,607

(22) Filed: Jun. 17, 2003

(65) Prior Publication Data

US 2004/0079168 A1 Apr. 29, 2004

(51) Int. Cl.[7] ............................................... G01N 3/00
(52) U.S. Cl. ........................................ 73/856; 73/821
(58) Field of Search ..................... 73/803, 812, 815, 73/818, 821, 841, 843, 845, 856

(56) References Cited

U.S. PATENT DOCUMENTS

| | | | | |
|---|---|---|---|---|
| 4,825,700 A | * | 5/1989 | Vardoulakis et al. | 73/749 |
| 4,845,995 A | * | 7/1989 | Kaste et al. | 73/794 |
| 4,854,175 A | * | 8/1989 | Budhu | 73/841 |
| 6,216,531 B1 | * | 4/2001 | Zhou | |

* cited by examiner

Primary Examiner—Max Noori
(74) Attorney, Agent, or Firm—Sheridan Ross PC

(57) ABSTRACT

An apparatus for direct shear stress testing of a sample includes a base plate, a supporting member, a fixing member, and a sliding member. The supporting member includes a supporting plate. The fixing member includes a stationary shear plate having a first receiving hole. The sliding member includes a movable shear plate interposed between and in sliding contact with the supporting plate and the stationary shear plate. The movable shear plate has a second receiving hole. The movable shear plate is slidable relative to the stationary shear plate to align the first and second receiving holes so as to receive the sample therein, and to misalign the first and second receiving holes so as to cause the sample to yield. The direct shear stress of the sample can thus be tested accordingly.

8 Claims, 5 Drawing Sheets

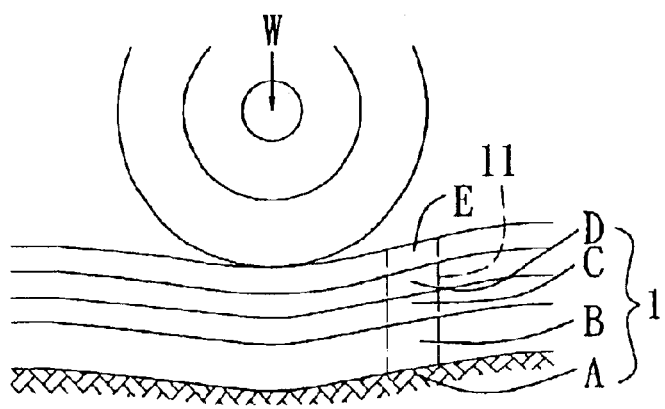
F I G. 1
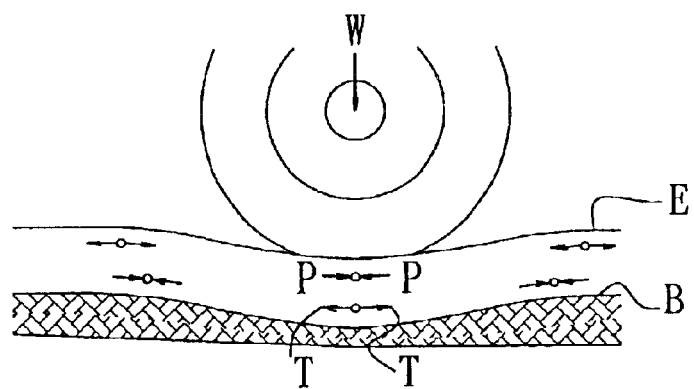
F I G. 2
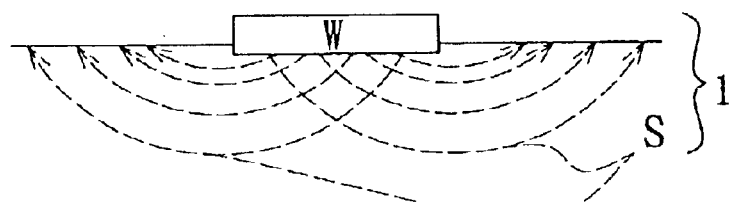
F I G. 3

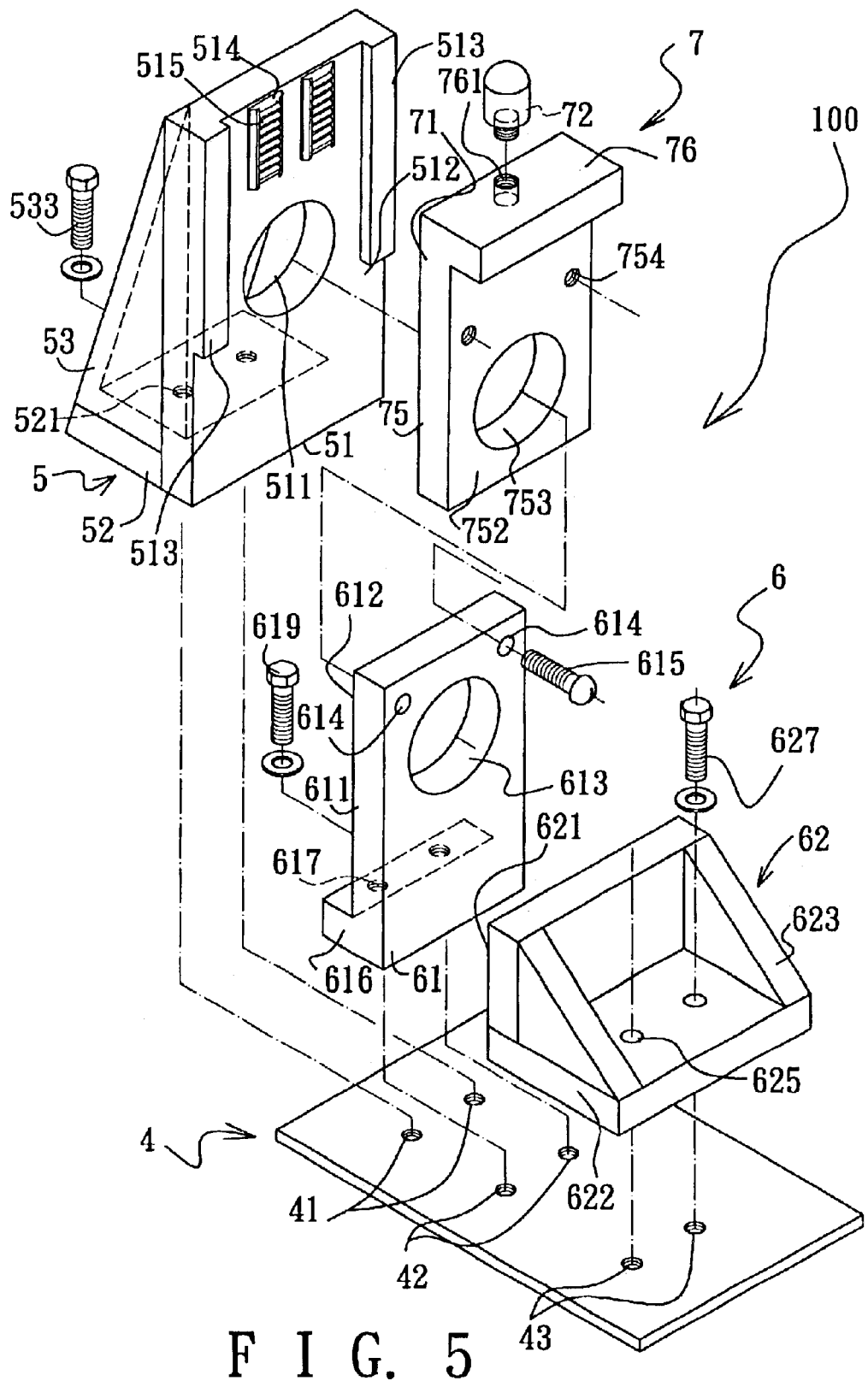
F I G. 5

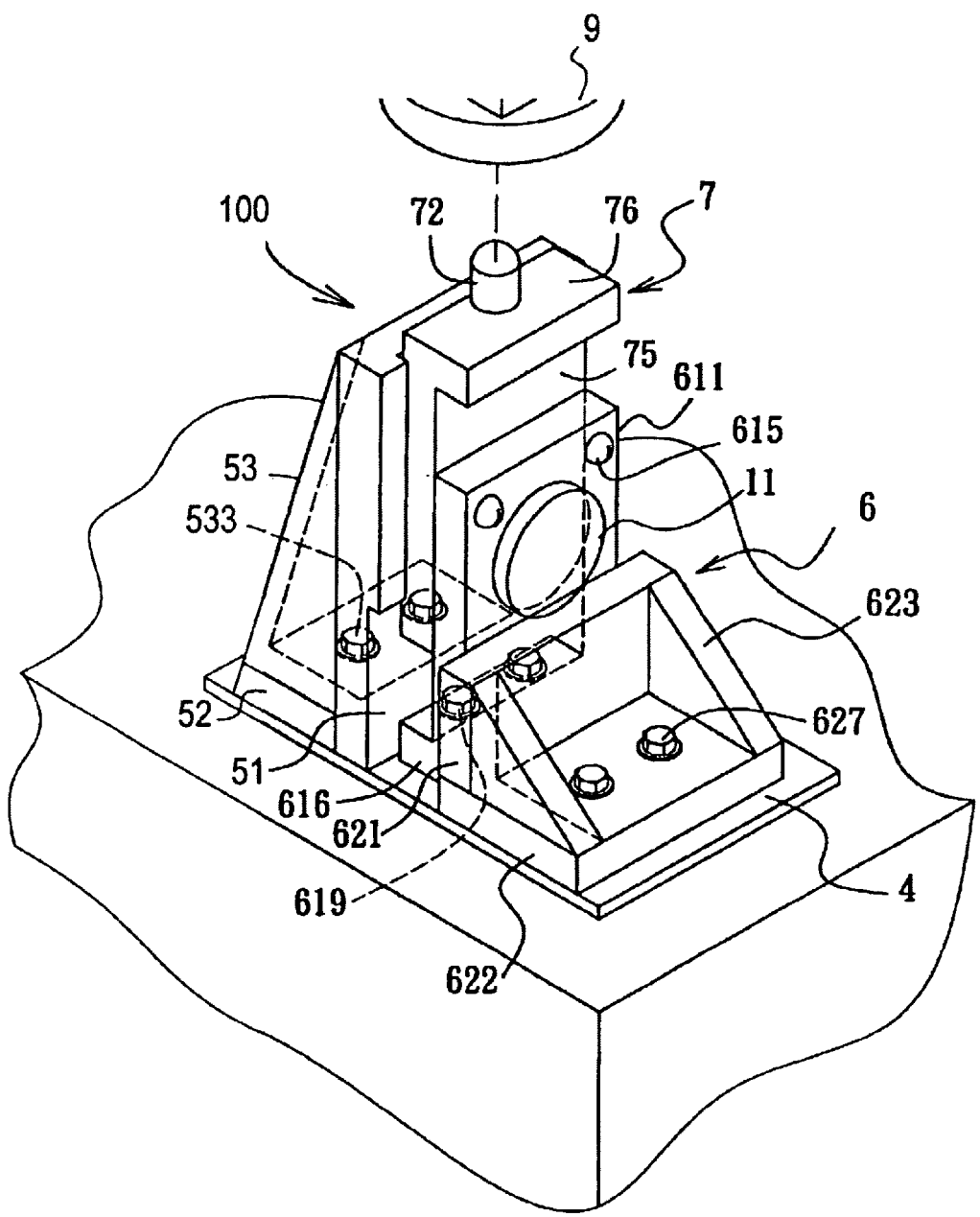
F I G. 7

APPARATUS FOR DIRECT SHEAR STRESS TESTING OF SAMPLE

BACKGROUND OF THE INVENTION

1. Field of the Invention

The invention relates to an apparatus for direct shear stress testing of a sample.

2. Description of the Related Art

Asphalt mixture can be applied in various fields, including road systems, airport runways, railway engineering, architecture engineering, and the like.

FIG. 1 illustrates a conventional asphalt pavement 1, which is made by blending asphalt cement as a binding material with various granular aggregate and fillers in a suitable proportion to produce asphalt mixture, and subsequently paving the asphalt mixture on a subgrade (A) in a laminar construction that includes a subbase course (B), a base course (C), a surface course (D), and a friction course (E). Each layer of the laminar construction has its own specific function. For example, the friction course (E) is the upper layer of the asphalt pavement 1, and is used to resist the friction imposed by wheels of vehicles, and to increase the friction between the asphalt pavement 1 and the wheels so as to enhance braking capability of vehicles. The subbase course (B) is used to transfer the load (w) imposed through vehicle wheels to the subgrade (A).

When the asphalt pavement 1 bears the load (W) imposed through one of the wheels of the vehicle, deformation of the asphalt pavement 1 will occur. Referring to FIG. 2, the asphalt pavement 1 is subjected to compressive force (P) at the upper part thereof, and to tensile force (T) at the lower part thereof simultaneously. Referring to FIG. 3, the asphalt pavement 1 also suffers from shear force (S) in a substantially transverse direction, which can result in breakage of the asphalt pavement 1.

In view of the aforesaid, in addition to the load (W), the asphalt pavement 1 is also subjected to compressive force (P), tensile force (T), and shear force (S) that result from kneading and impact of the vehicle wheels on the asphalt pavement 1. Therefore, it is a requirement for the asphalt pavement 1 to possess sufficient strength to bear various stress.

FIG. 4 illustrates a conventional shear box 2 for testing shear stress of a soil sample 20. The shear box 2 includes two cylindrical caps 22,24. The cylindrical caps 22,24 are mounted on opposite end portions of the soil sample 20, which is cylindrical in shape, and are held by a holding device (not shown). The maximum shear stress of the soil sample 20 can be detected by applying two opposite force (F) onto the cylindrical caps 22, 24 in a radial direction until the soil sample 20 breaks.

It is noted that the shear box 2 is merely used for detecting the shear stress of the soil sample 20, which has a relatively small bonding stress as compared to asphalt mixture. Therefore, the requirements for the conventional shear box 2 are not sufficient for shear stress testing of an asphalt mixture sample.

SUMMARY OF THE INVENTION

Therefore, it is an object of the present invention to provide an apparatus for direct shear stress testing of a sample, such as asphalt mixture, which has a relatively high strength, which is relatively stable when holding the sample, and which is easy to assemble and disassemble.

The apparatus according to this invention is adapted to be mounted on a worktable of a multi-functional compression machine for direct shear stress testing of a sample. The apparatus includes a base plate, a supporting member, a fixing member, and a sliding member. The base plate is adapted to be mounted on the worktable of the multi-functional compression machine. The supporting member is mounted on the base plate, and includes a supporting plate vertical to the base plate. The supporting plate has a supporting face. The fixing member includes a first fixing unit mounted on the base plate. The first fixing unit has a stationary shear plate which includes a first shear face parallel to and facing toward the supporting face of the supporting plate. The stationary shear plate further has a first receiving hole formed transversely through the first shear face. The sliding member includes a sliding unit which has a movable shear plate interposed between and in sliding contact with the supporting plate and the stationary shear plate. The movable shear plate has a second shear face in contact with the first shear face and a second receiving hole penetrating transversely through the second shear face.

The movable shear plate is slidable relative to the stationary shear plate to align the first and second receiving holes so as to receive the sample therein, and to misalign the first and second receiving holes so as to cause the sample to yield.

BRIEF DESCRIPTION OF THE DRAWINGS

Other features and advantages of the present invention will become apparent in the following detailed description of the preferred embodiment with reference to the accompanying drawings, of which:

FIG. 1 is a schematic view to illustrate the laminar construction of a conventional asphalt pavement;

FIG. 2 is a schematic view showing the distribution of compressive and tensile stress in the asphalt pavement when subjected to a load;

FIG. 3 is a schematic view showing the distribution of shear stress in the asphalt pavement when subjected to the load;

FIG. 5 is an exploded perspective view of the preferred embodiment of an apparatus for direct shear stress testing according to this invention;

FIG. 7 is a perspective view of the preferred embodiment when mounted on a multi-functional compression machine.

DETAILED DESCRIPTION OF THE PREFERRED EMBODIMENT

Figure 4:
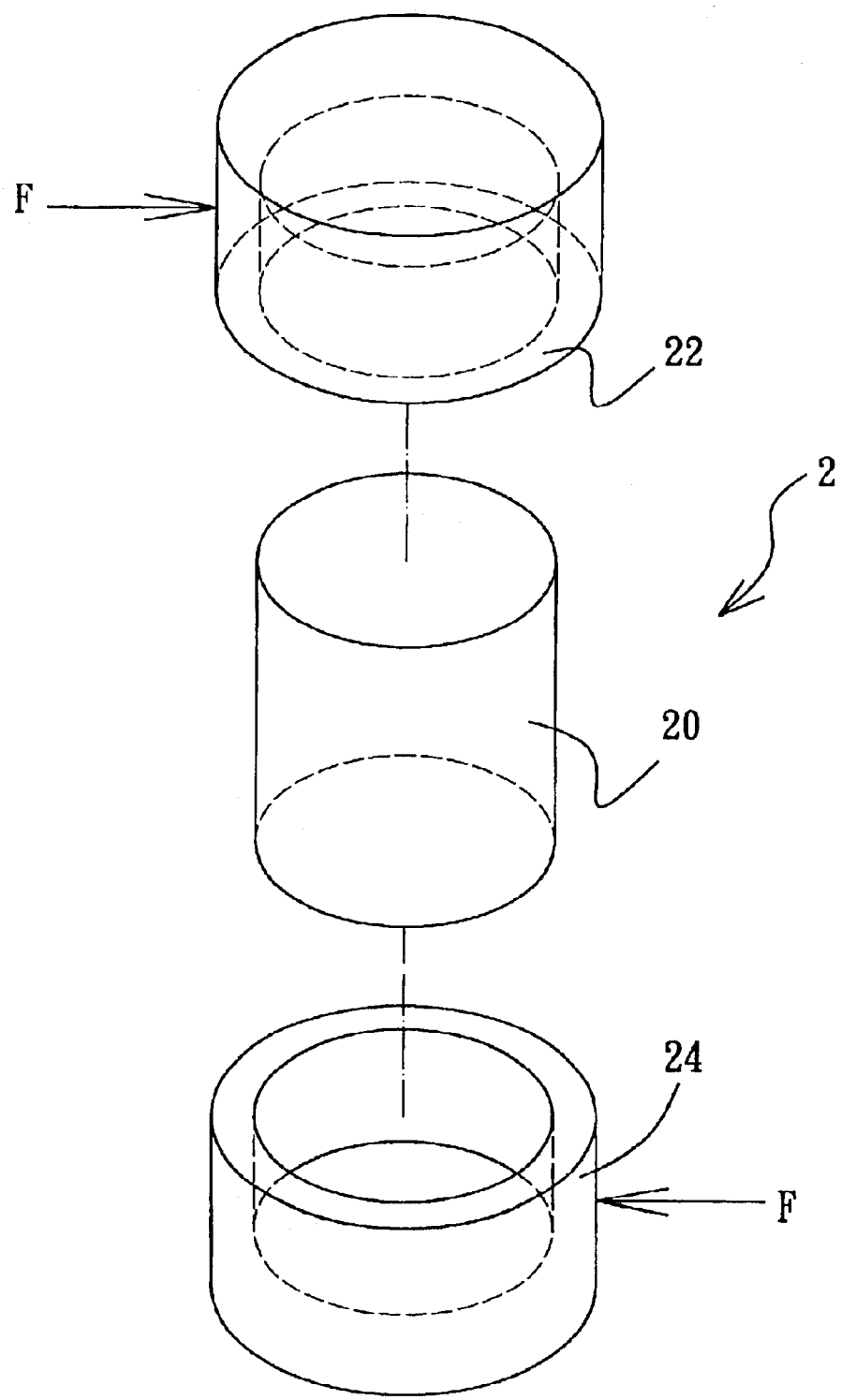
FIG. 4 is an exploded perspective view of a conventional shear box for testing a soil sample.
Figure 6:
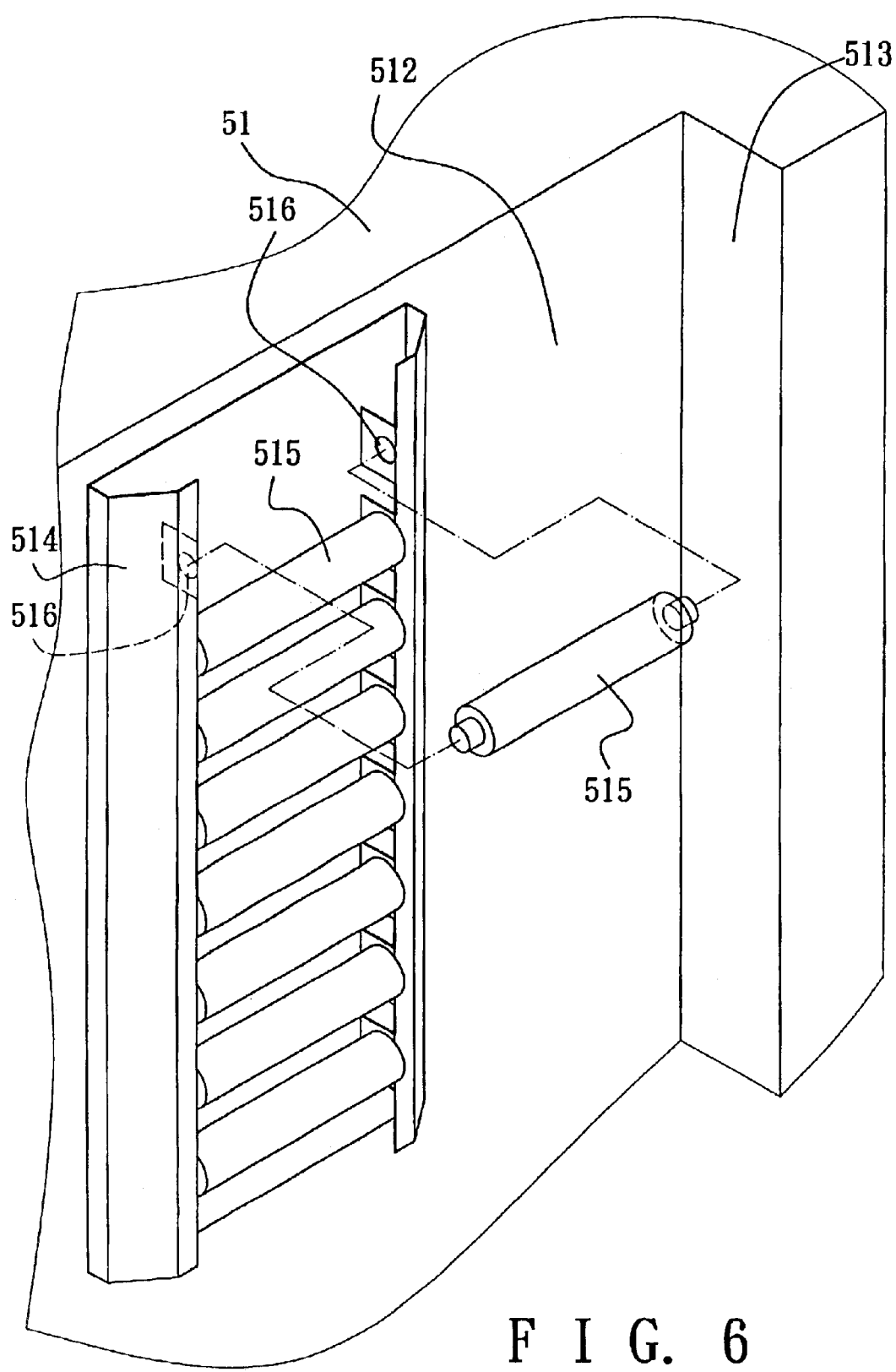
FIG. 6 is a fragmentary perspective view showing rolling units used in the preferred embodiment.

Referring to FIGS. 5, 6 and 7, the preferred embodiment of an apparatus 100 according to this invention is shown to be adapted to be mounted on a worktable 91 of a multi-functional compression machine 9 for direct shear stress testing of a sample 11, such as asphalt mixture. The apparatus 100 includes a base plate 4, a supporting member 5 mounted on the base plate 4, a fixing member 6, and a sliding member 7 interposed between and in sliding contact with the supporting member 5 and the fixing member 6.

The base plate 4 is adapted to be mounted on the worktable 91 of the multi-functional compression machine 9. The base plate 4 is in the form of a rectangular plate having a first set of tap holes 41 for screws 533 that mount the supporting member 5 on the base plate 4, and second and third sets of tap holes 42, 43 for screws 619, 627 that mount the fixing member 6 on the base plate 4.

The supporting member 5 is mounted on the base plate 4, and includes a supporting plate 51 vertical to the base plate 4. The supporting plate 51 has a supporting face 512. The supporting member 5 further includes a seat plate 52 mounted removably on the base plate 4 and protruding transversely from a bottom end of the supporting plate 51 opposite to the supporting face 512, and two triangular reinforcing plates 53, each of which is mounted vertically on a respective lateral side of the seat plate 52, and is fixed to the supporting plate 51. The seat plate 52 is provided with two holes 521 corresponding to the first set of tap holes 41.

The fixing member 6 includes a first fixing unit 61 mounted removably on the base plate 4. The first fixing unit 61 has a stationary shear plate 611 which includes a first shear face 612 parallel to and facing toward the supporting face 512 of the supporting plate 51. The stationary shear plate 611 further has a first receiving hole 613 formed transversely through the first shear face 612, preferably through the stationary shear plate 611.

The sliding member 7 includes a sliding unit 71 which has a movable shear plate 75 interposed between and in sliding contact with the supporting plate 51 and the stationary shear plate 611. The movable shear plate 75 has a second shear face 752 in contact with the first shear face 612 and a second receiving hole 753 penetrating transversely through the second shear face 752, preferably through the movable shear plate 75.

The movable shear plate 75 is slidable relative to the stationary shear plate 611 to align the first and second receiving holes 613, 753 so as to receive the sample 11 therein, and to misalign the first and second receiving holes 613, 753 so as to cause the sample 11 to yield. Additionally, the stationary and movable shear plates 611, 75 are provided respectively with retaining holes 614, 754 which are aligned when the first and second receiving holes 613, 753 are aligned. The retaining holes 614, 754 are adapted to receive a set of retaining elements 615 for temporarily fixing the movable shear plate 75 relative to the stationary shear plate 611. The sliding unit 71 of the sliding member 7 further includes a bearing plate 76 protruding from a top end of the movable shear plate 75 to extend over the stationary shear plate 611. The bearing plate 76 is provided with a tap hole 761. The sliding member 7 further includes a cap unit 72, which is mounted removably on the bearing plate 76 by means of threaded engagement in the tap hole 761, for receiving a compressive force from the multi-functional compression machine 9. The cap unit 72 is aligned vertically with the second receiving hole 753.

Moreover, the supporting member 5 further includes two parallel pivoting frames 514 spaced apart from each other and formed with a plurality of pairs of pivot holes 516. Each of a plurality of rolling units 515 is pivotally mounted on a corresponding pair of the pivot holes 516 and contacts the movable shear plate 75. The supporting plate 51 further has two parallel guiding flanges 513 protruding transversely from the supporting face 512 to receive the movable shear plate 75 therebetween.

The first fixing unit 61 of the fixing member 6 further includes a fixing plate 616 protruding transversely from a bottom end of the first shear face 611 and mounted removably on the base plate 4. The fixing plate 616 is provided with two holes 617 corresponding to the second pair of tap holes 42. The fixing member 6 further includes a second fixing unit 62 abutting against the first fixing unit 61 opposite to the first shear face 612 and mounted removably on the base plate 4. The second fixing unit 62 has a configuration similar to that of the supporting member 5, and includes a seat plate 622 mounted removably on the base plate 4, a supporting plate 621 vertically mounted on the seat plate 622, and two triangular reinforcing plates 623, each of which is mounted vertically on a respective lateral side of the seat plate 622, and is fixed to the supporting plate 621. The seat plate 622 is provided with two holes 625 corresponding to the third set of tap holes 43.

When assembling the apparatus 100, the base plate 4 is first mounted on the worktable 91 of the multi-functional compression machine 9. The supporting member 5 is then mounted on the base plate 4 by means of the screws 533 that extend through the holes 521 and that engage the tap holes 41. The first fixing unit 61 is then disposed on the base plate 4 such that the first shear face 612 faces toward the supporting face 512, and is fixed on the base plate 4 by means of the screws 619 that extend through the holes 617 and that engage the second pair of tap holes 42.

The sliding unit 71 is then interposed between the supporting plate 51 and the stationary shear plate 611 such that the second shear face 752 is in sliding contact with the first shear face 612 and such that the movable shear plate 75 is received between the guiding flanges 513. The retaining elements 615 are then received in the retaining holes 614, 754 for temporarily fixing the movable shear plate 75 relative to the stationary shear plate 611. The cap unit 72 is then mounted on the bearing plate 76 at the tap hole 761.

The second fixing unit 62 is then mounted on the base plate 4 such that the supporting plate 621 abuts against the stationary shear plate 611 of the first fixing unit 61. The second fixing unit 62 is then fixed on the base plate 4 by means of the screws 627 that extend through the holes 625 and that engage the third pair of the tap holes 43.

When the testing procedure is completed, the apparatus 100 can be disassembled by performing the above steps in a reverse order.

Since the apparatus 100 is assembled by screwing the individual components, such as the base plate 4, the supporting member 5, and the fixing member 6 on the worktable 91 of the multi-functional compression machine 9, the apparatus 100 can be assembled and disassembled with relative ease.

When the apparatus 100 is used for direct shear stress testing of the sample 11 (such as asphalt mixture), the apparatus 100 is adjusted on the worktable 91 of the multi-functional compression machine 9 so that a compressive member 92 of the multi-functional compression machine 9 is vertically aligned with the cap unit 72. The sample 11 is received in the first and second receiving holes 613, 753. The retaining elements 615 are then removed, and the compressive unit 92 presses against the cap unit 72 downwardly to enable the movable shear plate 75 to slide relative to the stationary shear plate 611 to cause the sample 11 to yield. The maximum shear stress of the sample 11 can be detected accordingly. By taking into consideration the dead load of the sliding unit 71, the shear stress of the sample 11 can be calculated.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

I claim:

1. An apparatus adapted to be mounted on a worktable of a multi-functional compression-machine for direct shear stress testing of a sample, comprising:

a base plate adapted to be mounted on the worktable of the multi-functional compression machine;

a supporting member mounted on said base plate, and including a supporting plate vertical to said base plate, said supporting plate having a supporting face;

a fixing member including a first fixing unit mounted on said base plate, said first fixing unit having a stationary shear plate which includes a first shear face parallel to and facing toward said supporting face of said supporting plate, said stationary shear plate further having a first receiving hole formed transversely through said first shear face; and a sliding member including a sliding unit which has a movable shear plate interposed between and in sliding contact with said supporting plate and said stationary shear plate, said movable shear plate having a second shear face in contact with said first shear face and a second receiving hole penetrating transversely through said second shear face, wherein said movable shear plate is slidable relative to said stationary shear plate to align said first and second receiving holes so as to receive the sample therein, and to misalign said first and second receiving holes so as to cause the sample to yield.

2. The apparatus as claimed in claim 1, wherein said supporting member further includes a plurality of rolling units mounted on said supporting face of said supporting plate to contact said movable shear plate.

3. The apparatus as claimed in claim 1, wherein said supporting member further includes a seat plate protruding transversely from a bottom end of said supporting plate opposite to said stationary shear plate, said seat plate being mounted removably on said base plate, said supporting plate further having two parallel guiding flanges protruding transversely from said supporting face to receive said movable shear plate therebetween.

4. The apparatus as claimed in claim 1, wherein said first fixing unit further includes a fixing plate protruding transversely from a bottom end of said first shear face and mounted removably on said base plate.

5. The apparatus as claimed in claim 1, wherein said fixing member further includes a second fixing unit abutting against said first fixing unit opposite to said first shear face and mounted removably on said base plate.

6. The apparatus as claimed in claim 1, wherein said stationary and movable shear plates are provided respectively with retaining holes which are aligned when said first and second receiving holes are aligned, said retaining holes being adapted to receive a retaining element for temporarily fixing said movable shear plate relative to said stationary shear plate.

7. The apparatus as claimed in claim 1, wherein said sliding unit of said sliding member further includes a bearing plate protruding from a top end of said movable shear plate to extend over said stationary shear plate, said sliding member further including a cap unit mounted removably on said bearing plate for receiving a compressive force from the multi-functional compression machine.

8. The apparatus as claimed in claim 7, wherein said cap unit is aligned vertically with said second receiving hole.

* * * * *